United States Patent [19] [11] 4,301,820
Cannell et al. [45] Nov. 24, 1981

[54] PERMANENT WAVING COMPOSITIONS CONTAINING FATTY ACID LACTYLATES AND GLYCOLATES AND THEIR METHOD OF USE

[75] Inventors: David W. Cannell, Los Angeles; Geoffrey R. Hawkins, Granada Hills, both of Calif.

[73] Assignee: Redken Laboratories, Inc., Canoga Park, Calif.

[21] Appl. No.: 118,231

[22] Filed: Feb. 4, 1980

[51] Int. Cl.³ .......................... A45D 7/04; A61K 7/09
[52] U.S. Cl. ............................................. 132/7; 424/72
[58] Field of Search ............................... 424/72; 132/7

[56] References Cited

U.S. PATENT DOCUMENTS 3,728,447  4/1973  Osipow et al. .......................... 424/70
3,910,289 10/1975  Wajaroff et al. .................. 424/70 X

FOREIGN PATENT DOCUMENTS 2749013  1/1978  Fed. Rep. of Germany ........ 424/72
45-28919  9/1970  Japan ..................................... 424/72
7303852  9/1973  Netherlands .......................... 424/72
1002889  9/1965  United Kingdom .................. 424/72

OTHER PUBLICATIONS

Sagarin, Cosm. Sci. & Tech., vol. 2, 1975, pp. 200, 210, 215 to 220.
Osipow et al., Drug & Cosmetic Industry, 4/1969, pp. 56, 58, 60, 62 & 151–153.

Primary Examiner—Dale R. Ore
Attorney, Agent, or Firm—Christie, Parker & Hale

[57] ABSTRACT

Fatty acid lactylates and/or glycolates are combined as humectant compounds with at least one reducing agent for hair and used in a permanent waving operation. In comparison to hair permanently waved without their use, the humectant compounds impart increased moisture retention to the hair without sacrificing waving efficiency while, in most instances, showing improved waving efficiencies, particularly at elevated humidities.

45 Claims, No Drawings

PERMANENT WAVING COMPOSITIONS CONTAINING FATTY ACID LACTYLATES AND GLYCOLATES AND THEIR METHOD OF USE

BACKGROUND OF THE INVENTION

Permanent waving is a process whereby a reducing agent is applied to the hair structure to open the disulfide linkages of the hair which are formed by the amino acid cystine. In the process, hair is wound onto an appropriate mandrel, e.g. roller or rod etc., prior to and/or following reduction with a suitable reducing agent. The protein chains flow under tension to assume the imparted shape. After rinsing, an oxidizing agent is then applied to re-establish or close the disulfide linkages which, in effect, hardens the protein structure to lock it into the new position.

Permanent waving may utilize a variety of reducing agents in a first step over a wide pH range. Depending upon pH, the waving process can be carried over a wide temperature range.

An essential element of a permanent waving composition is the reducing agent. Among the reducing agents are thioglycolic acid, salts, and esters thereof; thiolactic acid and salts thereof; alkali sulfides; alkali bisulfites, cysteine, and the like. The bulk of the reducing compositions are based on thioglycolic acid, salts, or esters thereof.

The hair may be waved with thioglycolates under acid conditions, where the pH will range from about 5.0 to about 6.9, preferably 6.5 to about 6.9. To this end, citric, lactic, phosphoric, and weak carboxylic acids are used as common acidifying agents. Acid waves based on thioglycolates utilize elevated temperatures up to about 140° F. using heat caps and hair dryers. Alkali bisulfite and bisulfide waves are also acid, namely at a pH from about 5.5 to 6.9, and are applied at room temperature.

Alkaline or "cold" wves are used at a pH in the range of 7.5 to 10.0 with ammonia, alkali carbonates and bicarbonates, ethanolamines, and alkali phosphates used as common alkalizing agents. Alkaline waves are also applied at room temperature.

The concentration of reducing agent, pH, and temperature are dictated by the hair condition, the time of processing desired, and the desired tightness of the curl.

Contact with the reducing agent may range from 10 minutes or less to 30 minutes or more. After an appropriate time with contact with the reducing agent, the reducing agent is rinsed from the hair, and an oxidizing agent is applied to close the disulfide bonds and set the hair. Excess oxidizing agent is then rinsed from the hair, and the hair dried. The most common oxidizing agents are hydrogen peroxide and bromate salts. Peroxides are applied over a pH range from 2.5 to about 4.0 and bromates from a pH of about 6.0 to about 8.0. Application is at ambient or elevated temperatures.

Independent of the type of permanent wave applied, moisture is deleterious to the appearance of a permanent wave. A substantial increase in moisture content of the hair over that which existed at the time the wave was applied will tend to cause the curl to drop and become limp. By contrast, when hair of desired moisture content is exposed to low relative humidities, the hair tends to lose moisture and become frizzy.

SUMMARY OF THE INVENTION

It has now been surprisingly found that the lactylates and glycolates, when incorporated as part of the reducing agent, composition or solution applied to hair, will impart unexpected and desirable qualities to the hair when processed through a permanent waving operation. They are useful in acid waving operations as well as alkaline waving operations. A most significant effect is that they serve as humectants to increase moisture retention of the hair and, under most conditions, increase waving efficiency. In particular, their use permits the hair to take up more moisture than with waving compositions used without them without a significant diminution in waving efficiency on exposure at elevated humidities. In most instances, waving efficiency is increased; and although waving efficiency is normally reduced as compared to conventional waving compositions at very low humidities, this is more than offset by the greater amount of moisture retention of the hair, which prevents frizziness.

The compositions provided in accordance with the instant invention comprise at least one hair reducing agent in combination with, as a humectant compound, at least one fatty acid lactylate and/or glycolate of the formula:

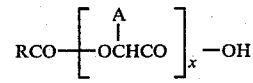

wherein RCO is an acyl radical of a fatty acid having from about 6 to about 22 carbon atoms, A is CH$_3$ or H, and x has a value of from 1 to about 4, as well as the ammonium, alkali metal, and amine salts thereof, the total of lactylates and/or glycolates added being sufficient to impart increased moisture retention to the hair but insufficient to have a substantial adverse effect on waving efficiency of the hair as compared to the quality of the permanent wave imparted using the same composition in the absence of a fatty acid lactylate and/or glycolate. The amine salts when used are the physiologically acceptable amine salts. The preferred composition contains an emulsifier to improve compability of the components of the permanent waving composition. Preferably the ratio of total moles of the reducing agent to total moles of lactylate and/or glycolate employed preferably ranges from about 15 to about 80. The fatty acid lactylates and/or glycolates are preferably combined with, during periods of storage, the reducing agent, which is then mixed with the balance of the components forming the reducing composition or solution at the time of use.

It is presently preferred that the reducing agent be thioglycolic acid, a salt thereof, or an ester thereof. Glycerolmonothioglycolate is presently preferred for acid compositions and ammonium thioglycolate for alkaline compositions. The presently preferred fatty acid lactylate is sodium isostearoyl-2-lactylate.

The permanent hair waving process of the invention includes the steps of contacting mandrel-shaped hair with a solution of a reducing agent for hair which includes at least one fatty acid, lactylate and/or glycolate to open the disulfide linkages of the hair and the step of subsequently closing the disulfide linkages of the hair by application of an oxidizing agent to the hair to set the hair in conformity with the shape of the mandrel.

In typical use, a reducing composition containing at least one reducing agent for hair and at least one fatty acid lactylate and/or glycolate is combined with the balance of the constituents forming a net reducing composition for application to the surface of hair in a conventional manner. After the wave is curled, and rinsed, the surface is oxidized using hydrogen peroxide or a bromate salt to set the curl. As is conventional, rinsing is employed following oxidation and the hair dried.

DETAILED DESCRIPTION

The present invention is based on the use of fatty acid, lactylates, and glycolates of the formula:

wherein RCO is the acyl radical of a fatty acid containing from about 6 to about 22 carbon atoms, A is $CH_3$ or H; and X is a number from 1 to about 4, as well as their ammonium, alkali metal, and physiologically acceptable amine salts, as humectants, introduced by acid or alkaline permanent waving solutions to impart moisture retention to the hair without having an adverse effect on waving efficiency.

The compounds useful in accordance with the present invention are described in greater detail in U.S. Pat. No. 3,728,447 to Osipow et al, incorporated herein by reference, and are produced by methods described in U.S. Pat. No. 3,733,252, also incorporated herein by reference.

Suitable fatty acid lactylates and glycolates which may be mentioned include isostearoyl-2-lactylate, caproyl-2-lactylate, caprylyl-2-lactylate, capryl-2-lactylate, lauryl-1-lactylate, lauryl-2-lactylate, lauryl-3-lactylate, lauryl-4-lactylate, myristyl-1-lactylate, myristyl-2-lactylate, oleoyl-2-lactylate, palmityl-2-lactylate, stearyl-2-lactylate, behenyl-2-lactylate, lauryl-1-glycolate, myristyl-1-glycolate, myristyl-2-glycolate, palmityl-1-glycolate, lauryl/myristyl-1-glycolate, capryl-1-glycolate; salts thereof, and the like. Sodium isostearoyl-2-lactylate is presently preferred.

The amount of lactylate and/or glycolate to be incorporated into the waving composition is an amount sufficient to impart increased moisture retention without an adverse effect on the waving efficiency of the hair as determined by standard tests as compared to the same reducing composition used without the lactylate and/or glycolate. This result will be achieved, in general, when the ratio of moles of the total of reducing agent to total moles of lactylate and/or glycolate present in the composition is from about 15 to about 80.

In accordance with the invention, the moisture retention of hair will be greater over the spectrum of relative humidities, while waving efficiency will be comparable to, greater than, or not significantly less than the waving efficiency achieved without the use of the humectant compound. In most instances, waving efficiency will be increased, particularly at elevated humidities.

Because the reduction compositions have been observed to separate on standing, it is desired to incorporate a minor amount of a emulsifier to stabilize the solution against separation. Emulsifiers, such as oleth-20, may be used and have been established not to have an adverse effect upon waving efficiency. With respect to acid waving solutions, as indicated above, the fatty acid lactylate and/or glycolates used are combined with the reducing agent, which forms one component of a two-component system. The second component normally used in forming the reducing composition is termed the balancer, and it is presently preferred that the balancer be an aqueous ammoniacal solution, preferably buffered. The component comprising the humectant compound reducing agent and, if present, the emulsifier, is then added to the balancer to provide a net solution at a suitable pH for application to the hair. For acid waves, the pH may range from 5.0 to 6-9, preferably from 6.5 to 6.9, and more preferably, 6.7 to 6.9. For alkaline waves, the pH may range from 7.5 to 10.0. In this instance, it is not necessary to employ a balancing solution and the compounds of this invention may be combined with the reducing agent and suitable alkalizing agent to be applied to the hair as a one-component system. As indicated, alkaline waves are applied at ambient temperature, whereas ambient and elevated temperature is used for acid waves, and temperatures up to 140° F. are conventionally employed. The hair is wound on a mandrel, e.g. rod, roller etc., in the conventional way, and the reducing composition of the invention is applied to the hair and allowed to soften the hair structure with attendant takeup of the lactylate and/or glycolate used. After exposure, with heating, if required, for about 10 to 20 minutes, preferably 15 minutes for acid wave compositions, as described in the attached examples, the excess reducing composition is rinsed from the hair, and a suitable oxidizer based on hydrogen peroxide or a bromate salt is applied to reset the cystine linkages. After thorough rinsing, the hair is dried to achieve a finished curl.

Although it is known from U.S. Pat. No. 3,728,447 that lactylates and glycolates are useful as hair conditioners, imparting substantivity to the hair, unusual effects have been found in their incorporation into permanent waving solutions:

(1) The most unusual effect, when used in both acid and alkaline or cold waves, is that the lactylates and/or glycolates, within the quantities specified above, normally impart a higher degree of waving efficiency than the same composition without the added lactylate and/or glycolate. This gives an initially tighter curl.

(2) With respect to rate of action, the use of the humectants of this invention have been established to increase the rate of penetration of the reducing solution into the individual hair strands such that processing time can be reduced by up to 25 percent.

(3) The greatest benefit, however, is the lactylates and/or glycolates cause hair to take up more moisture without causing the hair to become limp.

Curls permed with compositions used in accordance with the invention are less susceptible to relaxation at high humidity than curls formed when prepared with identical compositions which do not contain the lactylates and/or glycolates, despite the fact that more moisture is taken up by the hair. Because the hairs curled with the compositions of this invention hold more moisture at reduced humidities, as compared to hair curled without the added lactylates and/or glycolates, the tendency of the curl to frizz at reduced humidities is minimized.

In addition to providing higher waving efficiencies, and hair which holds a higher degree of moisture over a broad humidity range without any substantial diminution of waving efficiency, the lactylates and/or glycolates also impart greater manageability, sheen, and combability.

Moreover, they have been found, for the lifetime of the prepared solutions, to be fully compatible with the reactive chemicals present in alkaline and acidic hair waving compositions.

While nowise limiting, the following examples illustrate the instant invention.

In the ensuing Examples 1 to 21 and Controls A to J, there was used as the base system for reducing the hair a two-component system consisting of glycerolmonothioglycolate, termed herein GMTG, as the reductant, and as the balancer, a buffered 0.5% aqueous solution of ammonia. The test additives were incorporated into the GMTG. Prior to waving of the hair, the balancer was added to the GMTG in quantity to provide a reducing solution having a pH from about 6.7 to 6.9. The hair was processed and waving efficiency of the permed hair determined, following the procedures set forth in "The Chemistry and Manufacture of Cosmetics", 2nd Ed, Maison G. deNavarre, Continental Press (1975), pages 1211 to 1216. A dilute solution of hydrogen peroxide was used as the oxidant. Identical swatches of hair were used for each test conducted. Unless otherwise indicated, % increase in moisture is relative to the original dry hair sample as determined by the formula:

$$\frac{\text{Sample weight at given humidity} - \text{sample weight dry}}{\text{Sample weight dry}} \times 100$$

Dry hair is defined as hair at ambient temperature and humidity (40% to 50% RH) which would have a moisture content of 8% to 10% by weight.

CONTROL A and EXAMPLES 1 and 2

In the following control and examples, the hair was waved at a temperature of 62° C. for 10 minutes and waving efficiency determined.

|  | Reducing Composition | Waving Efficiency |
|---|---|---|
| Control A | 18 g. GMTG, 65 g. balancer | 40% |
| Example 1 | 18 g. GMTG, 1 g. ISL[a], 65 g. balancer | 49% |
| Example 2 | 18 g. GMTG, 2 g. ISL, 65 g. balancer | 47% |

[a] sodium isostearoyl-2-lactylate

Waving efficiencies using 18 g. GMTG, 3 g. ISL, and 65 g. balancer and 18 g. GMTG, 4 g. ISL, and 65 g. balancer were respectively 32% and 31%.

EXAMPLES 3 TO 5

Waving efficiencies as a function of waving time at 62° C. for composition containing 18.5 g. GMTG, 1 g. ISL, and 65 g. balancer were determined to be as follows:

|  | Time, min. | Waving Efficiency |
|---|---|---|
| Example 3 | 10 | 47% |
| Example 4 | 15 | 60% |
| Example 5 | 20 | 54% |

CONTROL B and EXAMPLES 6 and 7

As it was noted, the composition used for the above examples gave a slight separation on standing, it was determined whether the addition of an emulsifier, Ameroxol EO20, an oleth-20 manufactured by Amerchol, a unit of CPC Industries, Inc., adversely affect was efficiency. Waving occurred at 62° C. at a 15-minute waving time.

|  | Waving Composition | Waving Efficiency |
|---|---|---|
| Control B | 18 g. GMTG, 65 g. balancer | 47.5% |
| Example 6 | 18 g. GMTG, 1 g. ISL, 65 g. balancer | 51.5% |
| Example 7 | 18 g. GMTG, 1 g. ISL, 2 g. oleth-20, 65g. balancer | 52.5% |

It was concluded the emulsifier had no adverse effect on waving efficiency.

CONTROL C and EXAMPLES 9 to 11

To determine moisture pickup, hair samples were subjected to humidification at a level of 90% R.H. for 24 hours after being waved using, for Control C, a composition of 18 g. GMTG and 65 g. balancer; for example 9, the composition for Control C, plus 1 g. ISL; and for Examples 10 and 11, the composition for Example 9, plus 2 g. oleth-20. Respective moisture pickups were 0.37%, 4.16%, 8.6%, and 6.2%.

EXAMPLE 12

The hair samples of Examples 3 to 5 were placed in a humidifier maintained between 90% and 100% relative humidity for 72 hours. The respective moisture pickups were 37.5%, 31.96%, and 34.75%. Similarly, moisture pickup for Control A was 16.0%; the moisture pickup of Example 1 was 33.6%; and the moisture pickup of Example 2 was 31.7%. For the hair samples for which the reducing composition described above contained 3 g. ISL, moisture pickup of the hair was 25%, while the moisture pickup of the hair for the composition containing 4 g. ISL was 23%.

EXAMPLE 13

Four hair samples were waved using a composition composed of 18 g. GMTG, 1.5 g. ISL, 2 g. oleth-20, and 65 g. balancer, using 15 minutes at 62° C. for the reduction cycle. Initial waving efficiencies were 54%, 54.5%, 58%, and 58%, respectively. When exposed to 90% to 100% R.H. for 72 hours, moisture pickups were, respectively, 13.1%, 13.0%, 17.7%, and 14.3%. The hair samples were then re-evaluated for waving efficiency. The respective waving efficiencies were 51.5%, 53.0%, 53.0%, and 54.0% for an average loss of only 4%.

EXAMPLES 14 and 15 and CONTROLS D and E

Hair samples 14 and 15 were waved in the same manner as for Example 13. Hair samples for Controls D and E were waved in an identical manner, except that the ISL and emulsifier were omitted from the reducing composition. Table 1 below shows the initial weight of the hair samples and the % change in moisture contnt at the reported humidities for the times specified.

TABLE 1

|  | Initial Wt. (g) | 90% RH 24 hrs. | 60% RH after 2 hrs. more | 30% RH after 2.5 hrs. more | 25% RH after 6 hrs. |
|---|---|---|---|---|---|
| Example 14 | 12.191 | 19% | 4.6% | 2.7% | 0.27% |
| Example 15 | 12.116 | 17% | 5.3% | 3.5% | 0.27% |
| Control D | 18.925 | 14% | 4.3% | 3.3% | 0% |
| Control E | 20.877 | 16% | 4.2% | 1.95% | 0% |

EXAMPLES 16 and 17 and CONTROLS F and G

A composition containing 18 g. GMTG, 1 g. ISL, and 2 g. oleth-20 was used to prepare hair Examples 16 and 17. Following an identical procedure, Controls F and G were prepared, except that the ISL and emulsifier were omitted. Table 2 shows the initial waving efficiencies of the four hair swatches.

TABLE 2

|  | Waving Efficiency |
|---|---|
| Example 16 | 62.0% |
| Example 17 | 59.0% |
| Control F | 63.0% |
| Control G | 64.5% |

The four hair swatches were transferred to a humidifier and exposed to a relative humidity of 99% for 24 hours. Table 3 shows % moisture increase relative to the dry hair and change in waving efficiency.

TABLE 3

|  | % Moisture Increase | Waving Efficiency | Waving Efficiency Change |
|---|---|---|---|
| Example 16 | 8.5 | — | — |
| Example 17 | 6.9 | 52% | −7 |
| Average of 16 & 17 | 7.9 | — | — |
| Control F | 7.6 | 46% | −17 |
| Control G | 6.6 | — | — |
| Average of F & G | 7.1 | — | — |

Two swatches, Example 16 and Control G, were placed in a desiccator. Percent moisture was determined after exposure for 1 hour at 30% relative humidity; 6 hours at 10% relative humidity; 24 hours and 48 hours at 5% relative humidity, and waving efficiencies determined after the exposure to 5% relative humidity for 48 hours. The results are shown in table 4.

TABLE 4

|  | % Moisture | | | | Waving Efficiency | Waving Efficiency Change |
|---|---|---|---|---|---|---|
|  | 30% RH 1 hr. | 10% RH 6 hrs. | 5% RH 24 hrs. | 5% RH 48 hrs. | | |
| Example 16 | 4.03 | 2.06 | 1.67 | 0.360 | 49% | −13.0 |
| Control G | 3.14 | 1.83 | 1.07 | 0.356 | 56% | −8.5 |

It was concluded the greater loss in waving efficiency was due to the ability of the hair to hold more water in a dry climate, which has the positive effect of reducing the tendency of the hair to become frizzy.

EXAMPLES 18 and 19 and CONTROLS H and I

Four swatches of the same hair were permanent waved. Two (Examples 18 and 19) were waved using a solution of 18 g. GMTG, 1 g. ISL, 2 g. oleth-20, and 65 g. balancer. The other two (Controls H and I) were waved with the same solution, except the ISL and oleth-20 were omitted. Initial waving efficiencies, % moisture loss after desiccating at a relative humidity of 20% for 24 hours, and the effect on waving efficiency are shown in Table 5.

TABLE 5

|  | Initial Waving Efficiency | % Moisture Loss | Final Waving Efficiency | Waving Efficiency Change |
|---|---|---|---|---|
| Example 18 | 55% | 0.49 | 36% | −18 |
| Example 19 | 40% | 0.27 | 27% | −13 |
| Control H | 54% | 0.69 | 53% | −1 |
| Control I | 38% | 0.72 | 36% | −2 |

EXAMPLE 20

A hair swatch was waved using a composition containing 18 g. GMTG, 0.5 g. ISL, 2 g. oleth-20, and 65 g. balancer. The swatch was waved at 62° C. for 15 minutes. the initial weight of hair was 1.7062 g., and the initial waving efficiency was 50.56%.

The swatch was placed in a humidifier at 90% RH for 24 hours. Percent moisture uptake from original weight was 51.2%, and waving efficiency after 24 exposure hours at 90% RH was 44.21%. The swatch was then placed in low humidity desiccator (5% RH) for 24 hours. Moisture uptake was 3.12%, and waving efficiency was 42%. It was concluded the hair held water at both low and high humidities.

EXAMPLE 21 and CONTROL J determination by Iodine Staining of Perm Penetration There was used for this test a 0.1 N standardized iodine solution and European virgin blonde fibers, and a microscope capable of 250X magnification with calibrated reticle.

Standard salon procedures were followed. When test curl developed, further penetration was stopped by immediate rinsing in distilled water. Previously iodine-stained and perm-treated fibers were then mounted in distilled water on a microscope slide under 250X magnification, and the iodine boundary diameter ($D_B$) and final fiber diameter ($D_t$) was determined. The initial fiber diameter ($D_o$) was noted by similar procedure prior to waving solution application. The calculations in this test are:

$$\% \text{ Penetration} = \frac{D_o - D_B}{D_o} \times 100$$

$$\% \text{ Swelling} = \frac{D_t - D_o}{D_o} \times 100$$

For a sample wave (Example 21), using a reducing composition of 18 g. GMTG, 1 g. ISL, and 26 g. oleth-20 at a waving temperature of 60°–70° C., 100% penetration was achieved in 9 minutes, and swelling was 15%. The comparative sample (Control J) was waved using an otherwise identical composition, which did not contain ISL and oleth-20. One hundred percent penetration required 12 minutes, and swelling was 20%. This evidences that the composition containing ISL penetrated the hair at a rate 25% faster than one which did not contain ISL.

EXAMPLE 22 and CONTROL K

Two formulations were prepared to assess the effect of sodium isostearoyl-2-lactylate on a typical ammonium bisulfite waving system.

|  | Example 22 (% by wt.) | Control K (% by wt.) |
|---|---|---|
| Water | 86 | 87 |

|  | Example 22 (% by wt.) | Control K (% by wt.) |
|---|---|---|
| Oleth-20 | 3 | 3 |
| Sodium isostearoyl-2-lactylate | 1 | — |
| Ammonium bisulfite (45%) | 10 | 10 |
|  | 100 | 100 |
| Balancer, Aqueous ammonia | qs to pH 6.8 |  |

The two formulations were applied to brown hair in the conventional manner and processed for 15 minutes at ambient temperature. The tresses were rinsed and neutralized with a 6.0% solution of sodium bromate in water for 5 minutes. At the end of the neutralization, the samples were rinsed and suspended completely in distilled water for 15 minutes to equilibrate. Upon air drying, the following waving efficiencies were obtained:

Example 22—37%
Control K—25%

The lactylate at 1% by weight increased the waving efficiency of the bisulfite formula by 12%.

EXAMPLE 23 and CONTROL L

To a commercial alkaline wave at pH 9.5 was added 1 g. of sodium isostearoyl-2-lactylate (Example 25). The as provided alkaline wave was used for Control L. When hair was waved in the normal manner and neutralized with a 2.2% solution of hydrogen peroxide at pH 3.5, the following waving efficiencies were obtained:

Example 23—57%
Control L—51%

Example 23 and Control L were placed in a humodifier at 90% RH for 24 hours. The waving efficiencies were redetermined:

|  | Waving Efficiency | Waving Efficiency Change |
|---|---|---|
| Example 23 | 49% | −8 |
| Control L | 37% | −14 |

Example 23 and Control L were transferred to a dessicator for 24 hours. The waving efficiencies were redetermined:

|  | Waving Efficiency | Waving Efficiency Change |
|---|---|---|
| Example 23 | 41% | −8 |
| Control L | 36% | −1 |

EXAMPLE 24 and CONTROL M

To a commercial alkaline wave at pH 9.5 was added 1 g. of sodium isostearoyl-2-lactylate (Example 24). The as provided alkaline wave was used for Control M. The hair was waved in the normal manner and neutralized with a 2.2% solution of hydrogen peroxide at pH 3.5.

|  | Hair Weight Initial (g.) | Waving Efficiencies |
|---|---|---|
| Example 24 | 1.237 | 60% |
| Control M | 1.171 | 48% |

The two samples were placed in a 90% RH humidifier for 6 hours.

|  | % Moisture Gain | Waving Efficiency | Waving Efficiency Change |
|---|---|---|---|
| Example 24 | 54.2 | 55% | −5 |
| Control M | 45.0 | 41% | −7 |

The same samples were placed in a desiccator at 5% RH for 12 hours.

|  | % Moisture (relative to dry wt.) | Waving Efficiency | Waving Efficiency Change |
|---|---|---|---|
| Example 24 | 0.52 | 44% | −11 |
| Control M | −2.60 | 46% | +5 |

EXAMPLES 25, 26, 27, 28 and CONTROL N

In the following control and examples, the hair was waved at a temperature of 60° C. for 20 minutes. The waving agent for Control N was 18 g. of GMTG combined with 65 g. of balancer as described previously. The oxidizing agent was 103 g. of 2.2% hydrogen peroxide in water.

In each example, 1 g. of ISL and 2 g. of oleth-20 were added to various components of this acid waving system and nothing added to Control N. The initial waving efficiencies were determined.

|  |  | Waving Efficiency |
|---|---|---|
| Control N |  | 61% |
| Example 25 | (1 g. ISL, 2 G. oleth-20) | 66% |
| Example 26 | (1 g. ISL, 2 G. oleth-20 in 65 g. balancer) | 61% |
| Example 27 | (1 g. ISL, 2 G. oleth-20 in 103 g. oxidizing agent) | 63% |
| Example 28 | (1 g. ISL, 2 g. oleth-20 in both GMTG and oxidizing agent) | 54% |

This experiment demonstrates that the combination with the reducing agent alone provides the superior waving efficiency. The ISL in combination with the oxidizing agent yielded an improved efficiency relative to the control, but ISL in combination with both the reducing agent and oxidizing agent was inferior to the control.

Control N, Examples 25, 27 and 28 were placed in a humidifier at 90% RH for 6 hours. The samples were weighed and the efficiencies redetermined.

| Example No. | Original Weight | Weight at 90% RH | % Moisture Change |
|---|---|---|---|
| N | 1.1858 g. | 1.2523 g. | 5.60 |
| 25 | 1.2535 g. | 1.3562 g. | 8.20 |
| 27 | 1.4463 g. | 1.4547 g. | 0.58 |
| 28 | 1.3500 g. | 1.4113 g. | 4.50 |

Efficiencies after 6 hours at 90% RH

| Sample No. | Orig. Waving Efficiency | New Waving Efficiency | Waving Efficiency Change |
|---|---|---|---|
| N | 61% | 54% | −7 |
| 25 | 66% | 60% | −6 |
| 27 | 63% | 55% | −8 |

-continued

| | | | |
|---|---|---|---|
| 28 | 54% | 48% | −6 |

The samples were then transferred to a desiccator at 5% RH for 12 hours. They were reweighed and the efficiencies determined.

| Sample No. | Original Weight | Weight at 5% RH | % Moisture |
|---|---|---|---|
| N | 1.1858 | 1.1770 | −0.74 |
| 25 | 1.2535 | 1.2843 | +2.45 |
| 27 | 1.4463 | 1.4355 | −0.75 |
| 28 | 1.3500 | 1.3198 | −2.23 |

Efficiencies after 12 hours at 5% RH

| Sample No. | Orig. Waving Efficiency | New Waving Efficiency | Waving Efficiency Change |
|---|---|---|---|
| N | 61% | 60% | −1 |
| 25 | 66% | 53% | −13 |
| 27 | 63% | 66% | +3 |
| 28 | 54% | 53% | −1 |

These experiments confirm that ISL combined with the reducing agent is the preferred combination because it is able to retain moisture at both high and low humidity.

EXAMPLES 29, 30, 31 and CONTROL O

Same composition as other examples in which 1 g. of lactylate and 2 g. oleth-20 are combined with 18 g. of GMTG.

| | | Waving Efficiency |
|---|---|---|
| Control O | No lactylate | 54.5% |
| Example 29 | sodium isostearoyl-2-lactylate | 61.5% |
| Example 30 | sodium stearoyl-2-lactylate | 55.0% |
| Example 31 | sodium isostearoyl-1-lactylate | 47.0% |

These examples demonstrate the preference for the isostearoyl derivative over the straight chain stearoyl derivative and for the 2-lactylate over the 1-lactylate.

What is claimed is:

1. In a permanent waving composition for hair which contains at least one reducing agent for hair wherein the improvement comprises having in the permanent waving composition, at least one humectant compound selected from the group consisting of fatty acid lactylates and fatty acid glycolates of the formula:

wherein RCO is an acyl radical of a fatty acid having from about 6 to about 22 carbon atoms, A is $CH_3$ or H, and x has a value from 1 to about 4, and ammonium, alkali metal and amine salts thereof; the total amount of humectant compound included in said composition being sufficient to impart to hair, permanently waved using the composition, increased moisture retention and insufficient to have a substantial adverse affect on waving efficiency of the hair as compared to hair permanently waved using the composition in the absence of said humectant compound.

2. A composition as claimed in claim 1 in which the humectant compound is sodium isostearoyl-2-lactylate.

3. A composition as claimed in claim 2 in which the reducing agent is glycerolmonothioglycolate.

4. A composition as claimed in claim 1 in which an emulsifying agent is present.

5. A composition as claimed in claim 4 in which the emulsifying agent is oleth-20.

6. A composition as claimed in claim 3 in which an emulsifying agent is present.

7. A composition as claimed in claim 6 in which the emulsifying agent is oleth-20.

8. In a permanent waving composition for hair which contains at least one reducing aent for hair wherein the improvement comprises having in the permanent waving composition, at least one humectant compound selected from the group consisting of fatty acid lactylates and fatty acid glycolates of the formula:

wherein RCO is an acyl radical of a fatty acid having from about 6 to about 22 carbon atoms, A is $CH_3$ or H, and x has a value from 1 to about 4, and ammonium, alkali metal and amine salts thereof; the ratio of total moles of reducing agent to total moles of humectant compound in said composition being from about 15 to about 80.

9. A composition as claimed in claim 8 in which the humectant compound is sodium isostearoyl-2-lactylate.

10. A composition as claimed in claim 9 in which the reducing agent is glycerolmonothioglycolate.

11. A composition as claimed in claim 9 in which the reducing agent is ammonium bisulfite.

12. A composition as claimed in claim 7 in which an an emulsifying agent is present.

13. A composition as claimed in claim 12 in which the emulsifying agent is oleth-20.

14. A composition as claimed in claim 10 in which an emulsifying agent is present.

15. A composition as claimed in claim 14 in which the emulsifying agent is oleth-20.

16. In a two-component permanent waving system which provides a net reducing solution for hair, the first component of the system comprising at least one reducing agent for hair and the second component being a balancer for combination with the first component is preselected proportions to provide the net reducing solution having a select pH for application to hair, the improvement which comprises including in the first component at least one humectant compound selected from the group consisting of fatty acid lactylates and fatty acid glycolates of the formula:

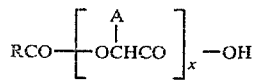

wherein RCO is an acyl radical of a fatty acid having from about 6 to about 22 carbon atoms, A is $CH_3$ or H, and x has a value from 1 to about 4, and ammonium, alkali metal and amines salts thereof; the total amount of humectant compound included in said first component being sufficient to impart to hair, permanent waved using the net reducing solution, increased moisture retention and insufficient to have a substantial adverse affect on waving efficiency of the hair as compared to hair permanently waved using the net reducing solution in the absence of said humectant compound.

17. A two-component permanent waving system as claimed in claim 16 in which the humectant compound is sodium isostearoyl-2-lactylate.

18. A two-component permanent waving system as claimed in claim 17 in which the reducing agent is glycerolmonothioglycolate.

19. A two-component permanent waving system as claimed in claim 16 in which the first component includes an emulsifying agent.

20. A two-component permanent waving system as claimed in claim 19 in which the emulsifying agent is oleth-20.

21. A two-component permanent waving system as claimed in claim 18 in which the first component includes an emulsifying agent.

22. A two-component permanent waving system as claimed in claim 21 in which the emulsifying agent is oleth-20.

23. A two-component permanent waving system as claimed in claim 16 in which the balancer is a buffered aqueous ammoniacal solution.

24. A two-component permanent waving system as claimed in claim 21 in which the balancer is a buffered aqueous ammoniacal solution.

25. In a two-component permanent waving system which provides a net reducing solution for hair, the first component of the system comprising at least one reducing agent for hair and the second component being a balancer for combination with the first component in preselected proportions to provide the net reducing solution having a select pH for application to hair; the improvement which comprises including in the first component at least one humectant compound selected from the group consisting of fatty acid lactylates and fatty acid glycolates of the formula:

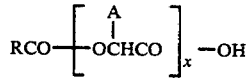

wherein RCO is an acyl radical of a fatty acid having from about 6 to about 22 carbon atoms, A is $CH_3$ or H, and x has a value from 1 to about 4, and ammonium, alkali metal and amine salts thereof; the ratio of total moles of reducing agent to total moles of humectant compound in said first component being from about 15 to about 80.

26. A two-component permanent waving system as claimed in claim 25 in which the humectant compound is sodium isostearoyl-2-lactylate.

27. A two-component permanent waving system as claimed in claim 26 in which the reducing agent is glycerolmonothioglycolate.

28. A two-component permanent waving system as claimed in claim 25 in which the first component includes an emulsifying agent.

29. A two-component permanent waving system as claimed in claim 28 in which the emulsifying agent is oleth-20.

30. A two-component permanent waving system as claimed in claim 27 in which the first component includes an emulsifying agent.

31. A two-component permanent waving system as claimed in claim 30 in which the emulsifying agent is oleth-20.

32. A two-component permanent waving system as claimed in claim 25 in which the balancer is a buffered aqueous ammoniacal solution.

33. A two-component permanent waving system as claimed in claim 30 in which the balancer is a buffered aqueous ammoniacal solution.

34. In a process for the permanent waving of hair which includes the steps of contacting mandrel-shaped hair with a solution of a reducing agent for hair to open the disulfide linkages of the hair and the step of closing the disulfide linkages of the mandrel-shaped hair by application of an oxidizing agent to the hair to set the hair in conformity with the shape of the mandrel; the improvement which comprises including in the solution of said reducing agent for hair at least one humectant compound selected from the group consisting of fatty acid lactylates and fatty acid glycolates of the formula:

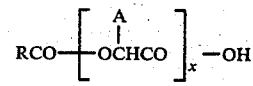

wherein RCO is an acyl radical of a fatty acid having from about 6 to about 22 carbon atoms, A is $CH_3$ or H, and x has a value from about 1 to about 4, and ammonium, alkali metal and amine salts thereof; the total amount of humectant compound included in said solution of a reducing agent for hair being sufficient to impart to hair, permanently waved in the process, increased moisture retention and insufficient to have a substantial adverse effect on waving efficiency of the hair as compared to hair permanently waved by the process using the solution of the reducing agent for hair in the absence of said humectant compound.

35. A process as claimed in claim 34 in which the humectant compound is sodium isostearoyl-2-lactylate.

36. A process as claimed in claim 34 in which said solution of a reducing agent for hair contains an emulsifier.

37. A process as claimed in claim 36 in which the emulsifier is oleth-20.

38. A process as claimed in claim 35 in which said solution of a reducing agent for hair contains an emulsifier.

39. A process as claimed in claim 38 in which the emulsifier is oleth-20.

40. In a process for the permanent waving of hair which includes the steps of contacting mandrel-shaped hair with a solution of a reducing agent for hair to open the disulfide linkages of the mandrel-shaped hair by application of an oxidizing agent to the hair to set the hair in conformity with the shape of the mandrel; the improvement which comprises including in the solution of said reducing agent for hair at least one humectant compound selected from the group consisting of fatty acid lactylates and fatty acid glycolates of the formula:

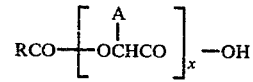

wherein RCO is an acyl radical of a fatty acid having from about 6 to about 22 carbon atoms, A is CH$_3$ or H, and x has a value from 1 to about 4, and ammonium, alkali metal and amine salts thereof; wherein the ratio of total moles of reducing agent to total moles of humectant compound in the solution of said reducing agent is about 15 to about 80.

41. A composition as claimed in claim 40 in which the humectant compound is sodium isostearoyl-2-lactylate.

42. A process as claimed in claim 40 in which said solution of a reducing agent for hair contains an emulsifier.

43. A process as claimed in claim 42 in which the emulsifier is oleth-20.

44. A process as claimed in claim 41 in which said solution of a reducing agent for hair contains an emulsifier.

45. A process as claimed in claim 44 in which the emulsifier is oleth-20.

* * * * *

UNITED STATES PATENT AND TRADEMARK OFFICE
CERTIFICATE OF CORRECTION

PATENT NO. : 4,301,820
DATED : November 24, 1981
INVENTOR(S) : David W. Cannell
Geoffrey R. Hawkins It is certified that error appears in the above-identified patent and that said Letters Patent are hereby corrected as shown below:

```
     Column 1, line 41, "wves" should read -- waves --.
Column 6, line 1, "was" should read -- wave --; line 44,
"54.5%" should read -- 51.5% --; line 58, "contnt" should
read -- content --.  Column 8, line 14, "the" should read
-- The --.  Column 9, line 34, "humodifier" should read
-- humidifier --; line 59, "asprovided" should read
-- as-provided --.  Column 12, line 14, "aent" should read
-- agent --; line 68, "permanent" should read -- permanently --.
```

Signed and Sealed this

First Day of March 1983

[SEAL]

Attest:

GERALD J. MOSSINGHOFF

Attesting Officer      Commissioner of Patents and Trademarks